(12) United States Patent
Kamenoue et al.

(10) Patent No.: US 12,030,844 B2
(45) Date of Patent: *Jul. 9, 2024

(54) COMPOUND AND COMPOSITION

(71) Applicant: KAO CORPORATION, Tokyo (JP)

(72) Inventors: Shogo Kamenoue, Wakayama (JP); Takashi Mizooku, Tokyo (JP); Ryuya Arata, Wakayama (JP); Akiyoshi Kimura, Wakayama (JP)

(73) Assignee: KAO CORPORATION, Tokyo (JP)

( * ) Notice: Subject to any disclaimer, the term of this patent is extended or adjusted under 35 U.S.C. 154(b) by 384 days.

This patent is subject to a terminal disclaimer.

(21) Appl. No.: 17/605,705

(22) PCT Filed: May 28, 2020

(86) PCT No.: PCT/JP2020/021174
§ 371 (c)(1),
(2) Date: Oct. 22, 2021

(87) PCT Pub. No.: WO2020/241771
PCT Pub. Date: Dec. 3, 2020

(65) Prior Publication Data
US 2022/0144741 A1    May 12, 2022

(30) Foreign Application Priority Data
May 28, 2019 (JP) ................. 2019-099445

(51) Int. Cl.
*C07C 43/13*      (2006.01)
*C07D 303/14*     (2006.01)

(52) U.S. Cl.
CPC ............ *C07C 43/13* (2013.01); *C07D 303/14* (2013.01)

(58) Field of Classification Search
CPC ..... C07C 43/13; C07C 43/132; C07D 303/14; C10M 2207/046; C10M 129/16; C10M 2207/09; C09D 5/00; C09D 7/63; C08K 5/06
USPC ............................ 106/13; 166/270; 508/583
See application file for complete search history.

(56) References Cited

U.S. PATENT DOCUMENTS

| | | | |
|---|---|---|---|
| 3,639,240 A | 2/1972 | Mutchler | |
| 4,465,866 A | 8/1984 | Takaishi et al. | |
| 4,719,084 A | 1/1988 | Schmid et al. | |
| 5,429,820 A | 7/1995 | Kamitani et al. | |
| 5,614,268 A | 3/1997 | Varley et al. | |
| 6,387,867 B1 | 5/2002 | Ishikawa et al. | |
| 9,296,942 B2 | 3/2016 | Weerasooriya et al. | |
| 10,045,529 B2 | 8/2018 | Griese et al. | |
| 11,702,584 B2* | 7/2023 | Kamenoue | C07C 41/03 166/270.1 |
| 11,725,143 B2* | 8/2023 | Kamenoue | C07C 41/03 508/579 |
| 11,739,039 B2* | 8/2023 | Kamenoue | C09K 8/584 166/270.1 |
| 11,781,084 B2* | 10/2023 | Kamenoue | C10M 129/08 508/583 |
| 2001/0012821 A1 | 8/2001 | Koishikawa et al. | |
| 2002/0025295 A1 | 2/2002 | Kim | |
| 2004/0266647 A1 | 12/2004 | Kubo et al. | |
| 2005/0037931 A1 | 2/2005 | Rowland et al. | |
| 2007/0155635 A1 | 7/2007 | Tagawa et al. | |
| 2010/0056821 A1 | 3/2010 | Ohtawa et al. | |
| 2010/0222603 A1* | 9/2010 | Selifonov | A01N 25/30 549/453 |
| 2010/0274039 A1 | 10/2010 | Choi et al. | |
| 2011/0212880 A1 | 9/2011 | Inoue et al. | |
| 2014/0298577 A1 | 10/2014 | Burt et al. | |

(Continued)

FOREIGN PATENT DOCUMENTS

| | | |
|---|---|---|
| CN | 1826400 A | 8/2006 |
| CN | 101412566 A | 4/2009 |

(Continued)

OTHER PUBLICATIONS

English translation of the Chinese Search Report for Chinese Application No. 202080020056.7, dated Oct. 25, 2023.
English translation of the Chinese Search Report for Chinese Application No. 202080032095.9, dated Oct. 12, 2023.
Stropoli et al., "Assessing Potential Oligomerization Reaction Mechanisms of Isoprene Epoxydiols on Secondary Organic Aerosol," Environmental Science & Technology, vol. 53, No. 1, 2019, pp. 176-184.
International Preliminary Report on Patentability and English translation of the Written Opinion of the International Searching Authority for International Application No. PCT/JP2020/021174, dated Dec. 9, 2021.

(Continued)

*Primary Examiner* — Prem C Singh
*Assistant Examiner* — Francis C Campanell
(74) *Attorney, Agent, or Firm* — Birch, Stewart, Kolasch & Birch, LLP

(57) ABSTRACT

The present invention provides: a compound that has a low melting point and is capable of forming a film of high hydrophobicity, and a composition containing this compound. The compound of the present invention is represented by chemical formula (1).

[Chemical Formula (1)]

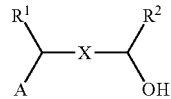

(In the formula, $R^1$ and $R^2$ are each a $C_1$-$C_{33}$ aliphatic hydrocarbon group, the total number of carbons of in $R^1$ and $R^2$ is 14-34, X is a single bond or a $C_1$-$C_5$ aliphatic hydrocarbon group, and A is —O—$CH_2$—CH(OH)—$CH_2$OH or —O—CH(—$CH_2$—OH)$_2$).

20 Claims, No Drawings

(56) References Cited

U.S. PATENT DOCUMENTS

| | | | |
|---|---|---|---|
| 2015/0005225 | A1 | 1/2015 | Tulchinsky et al. |
| 2015/0133353 | A1 | 5/2015 | Arai et al. |
| 2015/0191672 | A1 | 7/2015 | Hanyuda et al. |
| 2016/0100574 | A1 | 4/2016 | Pesaro et al. |
| 2018/0371360 | A1 | 12/2018 | Doi |
| 2018/0371362 | A1 | 12/2018 | Keuleers et al. |

FOREIGN PATENT DOCUMENTS

| | | | |
|---|---|---|---|
| CN | 101535230 | A | 9/2009 |
| CN | 101909744 | A | 12/2010 |
| CN | 102264884 | A | 11/2011 |
| CN | 103361651 | A | 10/2013 |
| CN | 104350137 | A | 2/2015 |
| CN | 107313271 | A | 11/2017 |
| CN | 108368453 | A | 8/2018 |
| CN | 108884575 | A | 11/2018 |
| JP | 53-137905 | A | 12/1978 |
| JP | 55-105632 | A | 8/1980 |
| JP | 62-235487 | A | 10/1987 |
| JP | 5-984 | A | 1/1993 |
| JP | 2002-235093 | A | 8/2002 |
| JP | 2007-146029 | A | 6/2007 |
| JP | 2008-506810 | A | 3/2008 |
| JP | 2010-260917 | A | 11/2010 |
| JP | 2012-506895 | A | 3/2012 |
| JP | 2014-25040 | A | 2/2014 |
| JP | 2015-501363 | A | 1/2015 |
| JP | 2015-124392 | A | 7/2015 |
| JP | 2016-56111 | A | 4/2016 |
| JP | 2016-148095 | A | 8/2016 |
| JP | 2017-197732 | A | 11/2017 |
| JP | 2018-104752 | A | 7/2018 |
| JP | 2018-172620 | A | 11/2018 |
| JP | 2019-6998 | A | 1/2019 |
| KR | 2001-0111811 | A | 12/2001 |
| WO | WO 00/43479 | A1 | 7/2000 |
| WO | WO 2005/018300 | A2 | 3/2005 |
| WO | WO 2007/062112 | A2 | 5/2007 |
| WO | WO 2010/049465 | A1 | 5/2010 |
| WO | WO 2013/062679 | A1 | 5/2013 |
| WO | WO 2017/090193 | A1 | 6/2017 |

OTHER PUBLICATIONS

International Preliminary Report on Patentability and English translation of the Written Opinion of the International Searching Authority for International Application No. PCT/JP2020/021194, dated Dec. 9, 2021.
International Preliminary Report on Patentability and English translation of the Written Opinion of the International Searching Authority for International Application No. PCT/JP2020/021208, dated Dec. 9, 2021.
International Preliminary Report on Patentability and English translation of the Written Opinion of the International Searching Authority for International Application No. PCT/JP2020/021211, dated Dec. 9, 2021.
International Preliminary Report on Patentability and English translation of the Written Opinion of the International Searching Authority for International Application No. PCT/JP2020/021213, dated Dec. 9, 2021.
"Synthesis and Application of Aliphatic Glycidyl Ethers," China Academic Journal Electronic Publishing House, 1995, pp. 15-21.
English translation of the Chinese Search Report for Chinese Application No. 202080030437.3, dated May 31, 2022.
Extended European Search Report for European Application No. 20812820.7, dated Jul. 1, 2022.
Extended European Search Report for European Application No. 20813026.0, dated Jul. 1, 2022.
Extended European Search Report for European Application No. 20813622.6, dated Jul. 1, 2022.
Extended European Search Report for European Application No. 20814785.0, dated Jun. 24, 2022.
Extended European Search Report for European Application No. 20813720.8, dated Jun. 30, 2023.
English translation of the Chinese Search Report for Chinese Application No. 202080032131.1, dated Aug. 23, 2022.
Lai et al., "Surfactants and Detergents," Advances in Fine Petrochemicals, vol. 11, No. 3, 1997, 53 pages total, with an English translation.
International Search Report for International Application No. PCT/JP2020/021174, dated Aug. 11, 2020.
International Search Report for International Application No. PCT/JP2020/021194, dated Aug. 18, 2020.
International Search Report for International Application No. PCT/JP2020/021208, dated Aug. 25, 2020.
International Search Report for International Application No. PCT/JP2020/021211, dated Aug. 18, 2020.
International Search Report for International Application No. PCT/JP2020/021213, dated Jul. 21, 2020.
U.S. Appl. No. 17/604,816, filed Oct. 19, 2021.
U.S. Appl. No. 17/605,729, filed Oct. 22, 2021.
U.S. Appl. No. 17/605,740, filed Oct. 22, 2021.
U.S. Appl. No. 17/605,921, filed Oct. 22, 2021.
English translation of the Chinese Search Report for Chinese Application No. 202080020092.3, dated Jan. 25, 2024.

* cited by examiner

COMPOUND AND COMPOSITION

TECHNICAL FIELD

The present invention relates to a compound and a composition containing the compound.

BACKGROUND ART

Ether alcohols obtained by reaction of an epoxy alkane with a polyhydric alcohol are useful as a raw material for an emulsifier, a surfactant, a dispersant, and the like.

For example, Patent Document 1 discloses ether alcohols obtained by reaction of an epoxy alkane having 8 to 20 carbon atoms with a mono- or polyfunctional alcohol having 1 to 10 carbon atoms and 1 to 4 alcoholic hydroxyl groups.

PRIOR ART DOCUMENTS

Patent Document

Patent Document 1: JP-A-55-105632

SUMMARY OF THE INVENTION

Problems to be Solved by the Invention

However, it has been found that the ether alcohols of Patent Document 1 have unfortunately so high melting point that they are poor in handleability, and a coating formed of the ether alcohol has low hydrophobicity.

The present invention has been made in view of the above circumstances, and provides a compound having a low melting point and capable of forming a coating having high hydrophobicity, and a composition containing the compound.

Means for Solving the Problems

As a result of intensive studies, the present inventors have found that the above problems can be solved by a compound having a specific structure.

The present invention relates to a compound represented by a Chemical Formula (1):

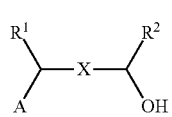
[Chemical Formula (1)]

wherein $R^1$ and $R^2$ are each an aliphatic hydrocarbon group having 1 or more and 33 or less carbon atoms, a total number of carbon atoms of $R^1$ and $R^2$ is 14 or more and 34 or less, X is a single bond or an aliphatic hydrocarbon group having 1 or more and 5 or less carbon atoms, and A is —O—CH$_2$—CH(OH)—CH$_2$OH or —O—CH(—CH$_2$—OH)$_2$.

Effect of the Invention

The compound represented by the Chemical Formula (1) of the present invention (hereinafter, also referred to as ether alcohol) is characterized by having a glyceryl ether group and a hydroxyl group inside the carbon chain, and having a low melting point. In addition, the ether alcohol of the present invention is excellent in formability of a hydrophobic coating.

MODE FOR CARRYING OUT THE INVENTION

Hereinafter, a detailed described is made of the present invention.

<Ether Alcohol>

The ether alcohol of the present invention is a compound represented by the following Chemical Formula (1). The ether alcohol of the present invention may contain at least one kind of a compound represented by the following Chemical Formula (1). The ether alcohol of the present invention may be composed of one or more kinds of a compound represented by the following Chemical Formula (1).

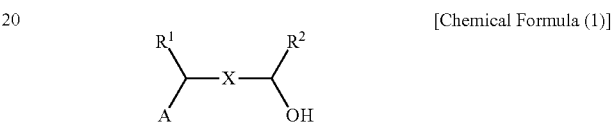
[Chemical Formula (1)]

(In Chemical Formula (1), $R^1$ and $R^2$ are each an aliphatic hydrocarbon group having 1 or more and 33 or less carbon atoms, a total number of carbon atoms of $R^1$ and $R^2$ is 14 or more and 34 or less, X is a single bond or an aliphatic hydrocarbon group having 1 or more and 5 or less carbon atoms, and A is —O—CH$_2$—CH(OH)—CH$_2$OH or —O—CH(—CH$_2$—OH)$_2$.)

$R^1$ and $R^2$ are each an aliphatic hydrocarbon group having 1 or more and 33 or less carbon atoms, preferably a linear alkyl group or a branched alkyl group (also referred to as a branched chain alkyl group), more preferably a linear alkyl group. The aliphatic hydrocarbon group may have a substituent such as a halogen group, a hydroxy group, a ketone group, a carboxy group, an aryl group, or an alkoxy group as long as the effect of the present invention is not impaired. $R^1$ and $R^2$ may be the same aliphatic hydrocarbon groups as each other or different aliphatic hydrocarbon groups from each other. In addition, the total number of substituents of $R^1$ and $R^2$ is preferably 5 or less, more preferably 3 or less, further preferably 1 or less, still more preferably 0 (that is, having no substituent) from the viewpoint of solubility in an organic solvent.

The total number of carbon atoms of $R^1$ and $R^2$ is 14 or more and 34 or less, or from the viewpoint of hydrophobicity, preferably 16 or more, or from the viewpoint of solubility in an organic solvent, preferably 22 or less, more preferably 20 or less, further preferably 18 or less, still more preferably 16 or less.

X is a single bond or an aliphatic hydrocarbon group having 1 or more and 5 or less carbon atoms, or from the viewpoint of production efficiency and ease of production, preferably a single bond or an aliphatic hydrocarbon group having 1 or more and 3 or less carbon atoms, more preferably a single bond or an aliphatic hydrocarbon group having 1 or more and 2 or less carbon atoms, further preferably a single bond or an aliphatic hydrocarbon group having 1 carbon atom, still more preferably a single bond.

The total number of carbon atoms of $R^1$, $R^2$, and X is 14 or more and 39 or less, or from the viewpoint of hydrophobicity, preferably 16 or more, or from the viewpoint of solubility in an organic solvent, preferably 31 or less, more preferably 28 or less, further preferably 26 or less, still more preferably 25 or less, still more preferably 24 or less, still more preferably 22 or less, still more preferably 20 or less, still more preferably 18 or less, still more preferably 16 or less.

When X is an aliphatic hydrocarbon group, from the viewpoint of production efficiency and ease of production, X is preferably a linear alkyl group or a branched alkyl group, more preferably a linear alkyl group.

From the viewpoint of production efficiency and ease of production, X is preferably
*—$(CH_2)_n$—* (n is 0 or more and 5 or less, and * represents a binding site),
wherein n is preferably 0 or more, preferably 3 or less, more preferably 2 or less, further preferably 1 or less, still more preferably 0, that is, a single bond.

From the viewpoint of production efficiency and ease of production, the ether alcohol preferably contains two or more kinds of the compound, between which the total numbers of carbon atoms of $R^1$ and $R^2$ are the same, but the numbers of carbon atoms of $R^1$ and the numbers of carbon atoms of $R^2$ are each different.

From the viewpoint of production efficiency and ease of production, the ether alcohol more preferably contains two or more kinds of the compound, between which the total numbers of carbon atoms of $R^1$, $R^2$ and X are the same, but the numbers of carbon atoms of $R^1$ and the numbers of carbon atoms of $R^2$ are each different.

From the viewpoint of production efficiency and ease of production, the ether alcohol more preferably contains two or more kinds of the compound in which X is a single bond or an aliphatic hydrocarbon group having 1 or more and 3 or less carbon atoms, and between which the total numbers of carbon atoms of $R^1$ and $R^2$ are the same, but the numbers of carbon atoms of $R^1$ and the numbers of carbon atoms of $R^2$ are each different.

From the viewpoint of production efficiency and ease of production, the ether alcohol more preferably contains two or more kinds of the compound in which X is a single bond or an aliphatic hydrocarbon group having 1 or more and 3 or less carbon atoms, and between which the total numbers of carbon atoms of $R^1$, $R^2$ and X are the same, but the numbers of carbon atoms of $R^1$ and the numbers of carbon atoms of $R^2$ are each different.

From the viewpoint of production efficiency and ease of production, the ether alcohol further preferably contains two or more kinds of the compound in which X is a single bond or an aliphatic hydrocarbon group having 1 or more and 2 or less carbon atoms, and between which the total numbers of carbon atoms of $R^1$ and $R^2$ are the same, but the numbers of carbon atoms of $R^1$ and the numbers of carbon atoms of $R^2$ are each different.

From the viewpoint of production efficiency and ease of production, the ether alcohol further preferably contains two or more kinds of the compound in which X is a single bond or an aliphatic hydrocarbon group having 1 or more and 2 or less carbon atoms, and between which the total numbers of carbon atoms of $R^1$, $R^2$ and X are the same, but the numbers of carbon atoms of $R^1$ and the numbers of carbon atoms of $R^2$ are each different.

From the viewpoint of production efficiency and ease of production, the ether alcohol still more preferably contains two or more kinds of the compound in which X is a single bond or an aliphatic hydrocarbon group having 1 carbon atom, and between which the total numbers of carbon atoms of $R^1$ and $R^2$ are the same, but the numbers of carbon atoms of $R^1$ and the numbers of carbon atoms of $R^2$ are each different.

From the viewpoint of production efficiency and ease of production, the ether alcohol still more preferably contains two or more kinds of the compound in which X is a single bond or an aliphatic hydrocarbon group having 1 carbon atom, and between which the total numbers of carbon atoms of $R^1$, $R^2$ and X are the same, but the numbers of carbon atoms of $R^1$ and the numbers of carbon atoms of $R^2$ are each different.

From the viewpoint of production efficiency and ease of production, the ether alcohol still more preferably contains two or more kinds of the compound in which X is a single bond, and between which the total numbers of carbon atoms of $R^1$ and $R^2$ are the same, but the numbers of carbon atoms of $R^1$ and the numbers of carbon atoms of $R^2$ are each different.

In the ether alcohol, the total content of the compound in which the total number of carbon atoms of $R^1$ and $R^2$ is 14 and the compound in which the total number of carbon atoms of $R^1$ and $R^2$ is 16 is preferably 75 mass % or more, more preferably 85 mass % or more, further preferably 95 mass % or more, still more preferably 100 mass %.

When the ether alcohol contains two or more kinds of the compound in which X is a single bond and between which the total numbers of carbon atoms of $R^1$ and $R^2$ are different, the total content of the compound in which the total number of carbon atoms of $R^1$ and $R^2$ is 14 and the compound in which the total number of carbon atoms of $R^1$ and $R^2$ is 16 is preferably 75 mass % or more, more preferably 85 mass % or more, further preferably 95 mass % or more, still more preferably 99 mass % or more, still more preferably 100 mass % from the viewpoint of solubility in an organic solvent.

When the ether alcohol contains two or more kinds of the compound between which the total numbers of carbon atoms of $R^1$ and $R^2$ are the same, but the numbers of carbon atoms of $R^1$ and the numbers of carbon atoms of $R^2$ are each different, the content ratio of the compound in which $R^1$ has 5 or more carbon atoms and $R^2$ has 5 or more carbon atoms is preferably 10 mass % or more, more preferably 20 mass % or more, further preferably 30 mass % or more, and preferably 90 mass % or less, more preferably 80 mass % or less, further preferably 70 mass % or less from the viewpoint of solubility in an organic solvent. In addition, from the viewpoint of the sustainability of foam, the content ratio of the compound in which $R^1$ has 5 or more carbon atoms and $R^2$ has 5 or more carbon atoms is preferably 30 mass % or less, more preferably 20 mass % or more and 30 mass % or less.

From the viewpoint of solubility in an organic solvent, the melting point of the ether alcohol is preferably 30° C. or lower, more preferably 20° C. or lower, further preferably 10° C. or lower, and may be −200° C. or higher.

The method for producing the ether alcohol is not particularly limited. For example, the ether alcohol can be produced by oxidizing the double bond in an internal olefin with a peroxide such as hydrogen peroxide, performic acid, or peracetic acid to synthesize an internal epoxide, and reacting the obtained internal epoxide with glycerin. In the case of a mixture in which the total numbers of carbon atoms of internal olefins are constant but the double bonds are present at different positions, the ether alcohol obtained by the above producing method is a mixture of a plurality of compounds in which X is a single bond and between which the total numbers of carbon atoms of $R^1$ and $R^2$ are the same, but the numbers of carbon atoms of $R^1$ and the numbers of carbon atoms of $R^2$ are each different. The ether alcohol obtained by the above producing method is usually a mixture of a compound 1 in which the A is —O—CH$_2$—CH(OH)—CH$_2$OH (hereinafter, also referred to as ether alcohol 1) and a compound 2 in which the A is —O—CH(—CH$_2$—OH)$_2$ (hereinafter, also referred to as ether alcohol 2). The content of the ether alcohol 1 in the mixture is preferably 1 mass % or more, more preferably 30 mass % or more, further preferably 40 mass % or more, still more preferably 50 mass % or more, and preferably 99 mass % or less, more preferably 90 mass % or less, further preferably 80 mass % or less, with respect to the total amount of the ether alcohol 1 and the ether alcohol 2.

The internal olefin used for the production of the ether alcohol may contain a terminal olefin. In this case, the content of terminal olefin contained in olefin is, for example, 0.1 mass % or more, 0.2 mass % or more, and 5 mass % or less, 3 mass % or less, 2 mass % or less, 1 mass % or less, 0.5 mass % or less.

The ether alcohol can be obtained as one kind of the compound represented by the Chemical Formula (1), a mixture of two or more kinds of the compound represented by the Chemical Formula (1), or a mixture of the above compound and a trace component other than olefin contained in the raw material olefin and a derivative thereof.

<Composition>

The composition of the present invention contains at least one kind of the ether alcohols.

The total content of the ether alcohol in the composition is not particularly limited, but is preferably 50 mass % or more, more preferably 60 mass % or more, further preferably 70 mass % or more, still more preferably 80 mass % or more, still more preferably 100 mass % from the viewpoint of reducing the transportation and storage costs.

When the composition contains the ether alcohol 1 and the ether alcohol 2, the content of the ether alcohol 1 is preferably 1 mass % or more, more preferably 30 mass % or more, further preferably 40 mass % or more, still more preferably 50 mass % or more, and preferably 99 mass % or less, more preferably 90 mass % or less, further preferably 80 mass % or less with respect to the total amount of the ether alcohol 1 and the ether alcohol 2, from the viewpoint of providing a high adsorption power. From the same viewpoint, the content is preferably 1 to 99 mass %, more preferably 30 to 99 mass %, further preferably 40 to 90 mass %, still more preferably 50 to 80 mass %.

The composition may contain water, a solvent, or various additives from the viewpoint of ease of handling and storage stability.

The ether alcohol or the composition of the present invention is used, for example, as a raw material for a surfactant, an emulsifier, a dispersant, a polymer, a resin, and the like, an additive for an oil agent such as a lubricating oil, a paint additive, an agrochemical additive, a resin additive, a metal surface modifier, a cosmetic base material, a medical auxiliary, a fiber oil agent, a petroleum agent, a processing agent, a lubricant, a plasticizer, an emulsifier, a dispersant, an antifogging agent, an antistatic agent, and an antifoaming agent.

The present invention and preferred embodiments of the present invention are described below.

<1>

A compound represented by a Chemical Formula (1):

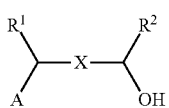

[Chemical Formula (1)]

wherein R$^1$ and R$^2$ are each an aliphatic hydrocarbon group having 1 or more and 33 or less carbon atoms, a total number of carbon atoms of R$^1$ and R$^2$ is 14 or more and 34 or less, X is a single bond or an aliphatic hydrocarbon group having 1 or more and 5 or less carbon atoms, and A is —O—CH$_2$—CH(OH)—CH$_2$OH or —O—CH(—CH$_2$—OH)$_2$.

<2>

A compound represented by a Chemical Formula (1):

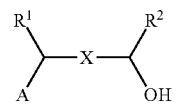

[Chemical Formula (1)]

wherein R$^1$ and R$^2$ are each an aliphatic hydrocarbon group having 1 or more and 33 or less carbon atoms, X is a single bond or an aliphatic hydrocarbon group having 1 or more and 5 or less carbon atoms, a total number of carbon atoms of R$^1$, R$^2$ and X is 14 or more and 39 or less, and A is —O—CH$_2$—CH(OH)—CH$_2$OH or —O—CH(—CH$_2$—OH)$_2$.

<3>

The compound according to <1> or <2>, wherein R$^1$ and R$^2$ are each a linear alkyl group or a branched alkyl group.

<4>

The compound according to <1> or <2>, wherein R$^1$ and R$^2$ are each a linear alkyl group.

<5>

The compound according to any one of <1> to <4>, wherein a total number of carbon atoms of R$^1$ and R$^2$ is preferably 16 or more, and preferably 22 or less, more preferably 20 or less, further preferably 18 or less, still more preferably 16 or less.

<6>

The compound according to any one of <1> to <4>, wherein a total number of carbon atoms of R$^1$ and R$^2$ is preferably 14 or more and 22 or less, more preferably 16 or more and 22 or less.

<7>

The compound according to any one of <1> to <4>, wherein a total number of carbon atoms of R$^1$ and R$^2$ is preferably 14 or more and 20 or less, more preferably 16 or more and 20 or less.

<8>

The compound according to any one of <1> to <4>, wherein a total number of carbon atoms of R$^1$ and R$^2$ is preferably 14 or more and 18 or less, more preferably 16 or more and 18 or less.

<9>

The compound according to any one of <1> to <4>, wherein a total number of carbon atoms of R$^1$ and R$^2$ is preferably 14 or more and 16 or less, more preferably 16.

<10>

The compound according to any one of <1> to <9>, wherein X is a single bond or an aliphatic hydrocarbon group having 1 or more and 3 or less carbon atoms.

<11>

The compound according to any one of <1> to <9>, wherein X is a single bond or an aliphatic hydrocarbon group having 1 or more and 2 or less carbon atoms.

<12>

The compound according to any one of <1> to <9>, wherein X is a single bond or an aliphatic hydrocarbon group having 1 carbon atom.

<13>
The compound according to any one of <1> to <9>, wherein X is a single bond.
<14>
The compound according to any one of <1> to <13>, wherein a total number of carbon atoms of $R^1$, $R^2$, and X is preferably 16 or more, and preferably 31 or less, more preferably 28 or less, further preferably 26 or less, still more preferably 25 or less, still more preferably 24 or less, still more preferably 22 or less, still more preferably 20 or less, still more preferably 18 or less, still more preferably 16 or less.
<15>
The compound according to any one of <1> to <14>, wherein X is preferably a linear alkyl group or a branched alkyl group, more preferably a linear alkyl group.
<16>
The compound according to any one of <1> to <14>, wherein X is preferably
*—$(CH_2)_n$—* (n is 0 or more and 5 or less, and * represents a binding site),
wherein n is preferably 0 or more, preferably 3 or less, more preferably 2 or less, further preferably 1 or less, still more preferably 0, that is, a single bond.
<17>
The compound according to any one of <1> to <16>, wherein the compound represented by the Chemical Formula (1) comprises two or more kinds of the compound between which total numbers of carbon atoms of $R^1$ and $R^2$ are the same, but numbers of carbon atoms of $R^1$ and numbers of carbon atoms of $R^2$ are each different.
<18>
The compound according to any one of <1> to <16>, wherein the compound represented by the Chemical Formula (1) comprises two or more kinds of the compound in which X is a single bond or an aliphatic hydrocarbon group having 1 or more and 3 or less carbon atoms, and between which the total numbers of carbon atoms of $R^1$ and $R^2$ are the same, but the numbers of carbon atoms of $R^1$ and the numbers of carbon atoms of $R^2$ are each different.
<19>
The compound according to any one of <1> to <16>, wherein the compound represented by the Chemical Formula (1) comprises two or more kinds of the compound in which X is a single bond or an aliphatic hydrocarbon group having 1 or more and 3 or less carbon atoms, and between which the total numbers of carbon atoms of $R^1$, $R^2$ and X are the same, but the numbers of carbon atoms of $R^1$ and the numbers of carbon atoms of $R^2$ are each different.
<20>
The compound according to any one of <1> to <16>, wherein the compound represented by the Chemical Formula (1) comprises two or more kinds of the compound in which X is a single bond or an aliphatic hydrocarbon group having 1 or more and 2 or less carbon atoms, and between which the total numbers of carbon atoms of $R^1$ and $R^2$ are the same, but the numbers of carbon atoms of $R^1$ and the numbers of carbon atoms of $R^2$ are each different.
<21>
The compound according to any one of <1> to <16>, wherein the compound represented by the Chemical Formula (1) comprises two or more kinds of the compound in which X is a single bond or an aliphatic hydrocarbon group having 1 or more and 2 or less carbon atoms, and between which the total numbers of carbon atoms of $R^1$, $R^2$ and X are the same, but the numbers of carbon atoms of $R^1$ and the numbers of carbon atoms of $R^2$ are each different.

<22>
The compound according to any one of <1> to <16>, wherein the compound represented by the Chemical Formula (1) comprises two or more kinds of the compound in which X is a single bond or an aliphatic hydrocarbon group having 1 carbon atom, and between which the total numbers of carbon atoms of $R^1$ and $R^2$ are the same, but the numbers of carbon atoms of $R^1$ and the numbers of carbon atoms of $R^2$ are each different.
<23>
The compound according to any one of <1> to <16>, wherein the compound represented by the Chemical Formula (1) comprises two or more kinds of the compound in which X is a single bond or an aliphatic hydrocarbon group having 1 carbon atom, and between which the total numbers of carbon atoms of $R^1$, $R^2$ and X are the same, but the numbers of carbon atoms of $R^1$ and the numbers of carbon atoms of $R^2$ are each different.
<24>
The compound according to any one of <1> to <16>, wherein the compound represented by the Chemical Formula (1) comprises two or more kinds of the compound in which X is a single bond, and between which the total numbers of carbon atoms of $R^1$ and $R^2$ are the same, but the numbers of carbon atoms of $R^1$ and the numbers of carbon atoms of $R^2$ are each different.
<25>
The compound according to any one of <1> to <16>, wherein in the compound represented by the Chemical Formula (1), a total content of the compound in which the total number of carbon atoms of $R^1$ and $R^2$ is 14 and the compound in which the total number of carbon atoms of $R^1$ and $R^2$ is 16 is preferably 75 mass % or more, more preferably 85 mass % or more, further preferably 95 mass % or more, still more preferably 100 mass %.
<26>
The compound according to any one of <1> to <16>, wherein the compound represented by the Chemical Formula (1) comprises two or more kinds of the compound in which X is a single bond and between which the total numbers of carbon atoms of $R^1$ and $R^2$ are different, the total content of the compound in which the total number of carbon atoms of $R^1$ and $R^2$ is 14 and the compound in which the total number of carbon atoms of $R^1$ and $R^2$ is 16 is preferably 75 mass % or more, more preferably 85 mass % or more, further preferably 95 mass % or more, still more preferably 99 mass % or more, still more preferably 100 mass %.
<27>
The compound according to any one of <1> to <24>, wherein the compound represented by the Chemical Formula (1) comprises two or more kinds of the compound between which the total numbers of carbon atoms of $R^1$ and $R^2$ are the same, but the numbers of carbon atoms of $R^1$ and the numbers of carbon atoms of $R^2$ are each different, the content ratio of the compound in which $R^1$ has 5 or more carbon atoms and $R^2$ has 5 or more carbon atoms is preferably 10 mass % or more, more preferably 20 mass % or more, further preferably 30 mass % or more, and preferably 90 mass % or less, more preferably 80 mass % or less, further preferably 70 mass % or less.
<28>
The compound according to any one of <1> to <24>, wherein the compound represented by the Chemical Formula (1) comprises two or more kinds of the compound between which the total numbers of carbon atoms of $R^1$ and $R^2$ are the same, but the numbers of carbon atoms of $R^1$ and the numbers of carbon atoms of $R^2$ are each different, the content ratio of the compound in which $R^1$ has 5 or more carbon atoms and $R^2$ has 5 or more carbon atoms is 10 mass % or more and 90 mass % or less.
<29>
The compound according to any one of <1> to <24>, wherein the compound represented by the Chemical Formula (1) comprises two or more kinds of the compound between which the total numbers of carbon atoms of $R^1$ and $R^2$ are the same, but the numbers of carbon atoms of $R^1$ and the numbers of carbon atoms of $R^2$ are each different, the content ratio of the compound in which $R^1$ has 5 or more carbon atoms and $R^2$ has 5 or more carbon atoms is 20 mass % or more and 80 mass % or less.
<30>
The compound according to any one of <1> to <24>, wherein the compound represented by the Chemical Formula (1) comprises two or more kinds of the compound between which the total numbers of carbon atoms of $R^1$ and $R^2$ are the same, but the numbers of carbon atoms of $R^1$ and the numbers of carbon atoms of $R^2$ are each different, the content ratio of the compound in which $R^1$ has 5 or more carbon atoms and $R^2$ has 5 or more carbon atoms is 30 mass % or more and 70 mass % or less.
<31>
The compound according to any one of <1> to <24>, wherein the compound represented by the Chemical Formula (1) comprises two or more kinds of the compound between which the total numbers of carbon atoms of $R^1$ and $R^2$ are the same, but the numbers of carbon atoms of $R^1$ and the numbers of carbon atoms of $R^2$ are each different, the content ratio of the compound in which $R^1$ has 5 or more carbon atoms and $R^2$ has 5 or more carbon atoms is 30 mass % or less.
<32>
The compound according to any one of <1> to <24>, wherein the compound represented by the Chemical Formula (1) comprises two or more kinds of the compound between which the total numbers of carbon atoms of $R^1$ and $R^2$ are the same, but the numbers of carbon atoms of $R^1$ and the numbers of carbon atoms of $R^2$ are each different, the content ratio of the compound in which $R^1$ has 5 or more carbon atoms and $R^2$ has 5 or more carbon atoms is 20 mass % or more and 30 mass % or less.
<33>
The compound according to any one of <1> to <32>, wherein a melting point of the compound represented by the Chemical Formula (1) is 30° C. or lower.
<34>
The compound according to any one of <1> to <32>, wherein a melting point of the compound represented by the Chemical Formula (1) is 20° C. or lower.
<35>
The compound according to any one of <1> to <32>, wherein a melting point of the compound represented by the Chemical Formula (1) is 10° C. or lower.
<36>
The compound according to any one of <1> to <35>, wherein the compound represented by the Chemical Formula (1) comprises a compound 1 in which A is —O—CH$_2$—CH(OH)—CH$_2$OH and a compound 2 in which A is —O—CH(—CH$_2$—OH)$_2$.
<37>
The compound according to <36>, wherein in the compound represented by Chemical Formula (1), a content of the compound 1 with respect to a total amount of the compound 1 and the compound 2 is preferably 1 mass % or more, more preferably 30 mass % or more, further preferably 40 mass % or more, still more preferably 50 mass % or more, and preferably 99 mass % or less, more preferably 90 mass % or less, further preferably 80 mass % or less.
<38>
The compound according to <36>, wherein in the compound represented by Chemical Formula (1), a content of the compound 1 with respect to a total amount of the compound 1 and the compound 2 is 1 mass % or more and 99 mass % or less.
<39>
The compound according to <36>, wherein in the compound represented by Chemical Formula (1), a content of the compound 1 with respect to a total amount of the compound 1 and the compound 2 is 30 mass % or more and 99 mass % or less.
<40>
The compound according to <36>, wherein in the compound represented by Chemical Formula (1), a content of the compound 1 with respect to a total amount of the compound 1 and the compound 2 is 40 mass % or more and 90 mass % or less.
<41>
The compound according to <36>, wherein in the compound represented by Chemical Formula (1), a content of the compound 1 with respect to a total amount of the compound 1 and the compound 2 is 50 mass % or more and 80 mass % or less.
<42>
The compound according to any one of <1> to <41>, wherein an internal olefin used for the production of the compound represented by Chemical Formula (1) contains a terminal olefin, a content of the terminal olefin contained in olefin is 0.1 mass % or more, or 0.2 mass % or more, and 5 mass % or less, 3 mass % or less, 2 mass % or less, 1 mass % or less, or 0.5 mass % or less.
<43>
The compound according to any one of <1> to <42>, wherein the compound represented by the Chemical Formula (1) is a reactant of an internal epoxide and glycerin.
<44>
The compound according to <43>, wherein the internal epoxide is an oxide of an internal olefin, and the internal olefin contains 0.5 mass % or less of a terminal olefin.
<45>
A composition comprising the compound according to any one of <1> to <44>.
<46>
The composition according to <45>, wherein a total content of the compound represented by the Chemical Formula (1) in the composition is preferably 50 mass % or more, more preferably 60 mass % or more, further preferably 70 mass % or more, still more preferably 80 mass % or more, still more preferably 100 mass %.
<47>
The composition according to <45> or <46>, wherein the composition contains the compound 1 and the compound 2, a content of the compound 1 is preferably 1 mass % or more, more preferably 30 mass % or more, further preferably 40 mass % or more, still more preferably 50 mass % or more, and preferably 99 mass % or less, more preferably 90 mass % or less, further preferably 80 mass % or less with respect to a total amount of the compound 1 and the compound 2.
<48>
The composition according to <45> or <46>, wherein the composition contains the compound 1 and the compound 2, a content of the compound 1 is preferably 1 to 99 mass %, more preferably 30 to 99 mass %, further preferably 40 to 90 mass %, still more preferably 50 to 80 mass % with respect to a total amount of the compound 1 and the compound 2.
<49>
The composition according to any one of <45> to <48>, further comprising water.

EXAMPLES

Hereinafter, a specific description is made of the present invention with reference to Examples. The content of each component is expressed in mass % unless otherwise indicated in Tables. Various measuring methods are as follows.
<Method for Measuring Double Bond Distribution in Olefin>
The double bond distribution in olefin was measured by gas chromatography (hereinafter, abbreviated as GC). Specifically, dimethyl disulfide was reacted with olefin to form a dithioated derivative, and then respective components were separated by GC. The double bond distribution in olefin was determined from respective peak areas. The apparatus used for measurement and analyzing conditions are as follows.
  GC apparatus: Trade name HP6890 (manufactured by Hewlett-Packard Company)
  Column: Trade name Ultra-Alloy-1 HT capillary column 30 m×250 μm×0.15 μm (manufactured by Frontier Laboratories, Ltd.)
  Detector: Hydrogen flame ion detector (FID)
  Injection temperature: 300° C.
  Detector temperature: 350° C.
  Oven: 60° C. (0 min.)→2° C./min.→225° C.→20° C./min.→350° C.→350° C. (5.2 min.)
<Method for Measuring Content Ratio of Structural Isomer>
Measurement was performed by $^1$H-NMR for a mixture of 0.05 g of alkyl glyceryl ether, 0.2 g of trifluoroacetic anhydride, and 1 g of deuterated chloroform. Measuring conditions are as follows.
  Nuclear magnetic resonance apparatus: Agilent 400-MR DD2, manufactured by Agilent Technologies, Inc.
  Observation range: 6410.3 Hz
  Data point: 65536
  Measurement mode: Presat
  Pulse width: 45°
  Pulse delay time: 10 sec
  Cumulative number: 128 times
<Production of Internal Olefin>

Production Example A1

(Production of Internal Olefin Having 16 Carbon Atoms (Internal Olefin 1))
A flask equipped with a stirrer was charged with 7000 g (28.9 mol) of 1-hexadecanol (Product name: KALCOL 6098, manufactured by Kao Corporation) and 700 g (10 wt % with respect to the raw material alcohol) of γ-alumina (STREM Chemicals, Inc.) as a solid acid catalyst, followed by reaction at 280° C. for 32 hours under stirring with circulation of nitrogen (7000 mL/min) in the system. The alcohol conversion after completion of the reaction was 100%, and the purity of C16 olefin was 99.6%. The obtained crude C16 internal olefin was transferred to a distiller, followed by distillation at 136 to 160° C./4.0 mmHg to yield an internal olefin 1 having an olefin purity of 100%. The double bond distribution in the obtained internal olefin 1 was 0.2% at the C1 position, 15.8% at the C2 position, 14.5% at the C3 position, 15.7% at the C4 position, 17.3% at the C5 position, 16.5% at the C6 position, and 20.0% at the C7 position and the C8 position in total.

Production Example A2

(Production of Internal Olefin Having 18 Carbon Atoms (Internal Olefin 2))
A reactor equipped with a stirrer was charged with 800 kg (3.0 kmol) of 1-octadecanol (Product name: KALCOL 8098, manufactured by Kao Corporation) and 80 kg (10 wt % with respect to the raw material alcohol) of activated alumina GP-20 (Mizusawa Industrial Chemicals, Ltd.) as a solid acid catalyst, followed by reaction at 280° C. for 16 hours under stirring with circulation of nitrogen (15 L/min) in the system. The alcohol conversion after completion of the reaction was 100%, and the purity of C18 olefin was 98.7%. The obtained crude C18 internal olefin was transferred to a distiller, followed by distillation at 163 to 190° C./4.6 mmHg to yield an internal olefin 2 having an olefin purity of 100%. The double bond distribution in the obtained internal olefin 2 was 0.3% at the C1 position, 13.3% at the C2 position, 12.6% at the C3 position, 13.9% at the C4 position, 14.8% at the C5 position, 13.7% at the C6 position, 12.6% at the C7 position, and 18.8% at the C8 position and the C9 position in total.

Production Example A3

(Production of Internal Olefin Having 14 Carbon Atoms (Internal Olefin 3))
An internal olefin 3 was obtained in the same manner as in Production Example A1 except that 28.9 mol of 1-tetradecanol (Product name: KALCOL 4098, manufactured by Kao Corporation) was used in place of 28.9 mol of 1-hexadecanol (Product name: KALCOL 6098, manufactured by Kao Corporation) for Production Example A1. The double bond distribution in the obtained internal olefin 3 was 1.3% at the C1 position, 31.8% at the C2 position, 23.8% at the C3 position, 21.0% at the C4 position, 8.5% at the C5 position, and 13.6% at the C6 position and C7 position in total.

Production Example A4

(Production of Internal Olefin Having 16 Carbon Atoms (Internal Olefin 4))
A flask equipped with a stirrer was charged with 7000 g (28.9 mol) of 1-hexadecanol (Product name: KALCOL 6098, manufactured by Kao Corporation) and 700 g (10 wt % with respect to the raw material alcohol) of γ-alumina (STREM Chemicals, Inc.) as a solid acid catalyst, followed by reaction at 280° C. for 3 hours under stirring with circulation of nitrogen (7000 mL/min) in the system. The alcohol conversion after completion of the reaction was 100%, and the purity of C16 olefin was 99.6%. The obtained crude C16 internal olefin was transferred to a distiller, followed by distillation at 136 to 160° C./4.0 mmHg to yield an internal olefin 4 having an olefin purity of 100%. The double bond distribution in the obtained internal olefin 4 was 2.2% at the C1 position, 27.0% at the C2 position, 20.5% at the C3 position, 16.4% at the C4 position, 11.8% at the C5 position, 9.9% at the C6 position, and 12.2% at the C7 position and the C8 position in total.

Production Example A5

(Production of Internal Olefin Having 18 Carbon Atoms (Internal Olefin 5))

A reactor equipped with a stirrer was charged with 800 kg (3.0 kmol) of 1-octadecanol (Product name: KALCOL 8098, manufactured by Kao Corporation) and 80 kg (10 wt % with respect to the raw material alcohol) of activated alumina GP-20 (Mizusawa Industrial Chemicals, Ltd.) as a solid acid catalyst, followed by reaction at 280° C. for 10 hours under stirring with circulation of nitrogen (15 L/min) in the system. The alcohol conversion after completion of the reaction was 100%, and the purity of C18 olefin was 98.2%. The obtained crude C18 internal olefin was transferred to a distiller, followed by distillation at 163 to 190° C./4.6 mmHg to yield an internal olefin 5 having an olefin purity of 100%. The double bond distribution in the obtained internal olefin 5 was 2.0% at the C1 position, 24.3% at the C2 position, 19.2% at the C3 position, 16.0% at the C4 position, 11.9% at the C5 position, 9.3% at the C6 position, 7.5% at the C7 position, and 9.8% at the C8 position and the C9 position in total.

<Production of Internal Epoxide>

Production Example B1

(Production of Internal Epoxide Having 16 Carbon Atoms (Internal Epoxide 1))

A flask equipped with a stirrer was charged with the internal olefin 1 (800 g, 3.56 mol) obtained in Production Example A1, 107 g (1.78 mol) of acetic acid (manufactured by Wako Pure Chemical Industries, Ltd.), 15.6 g (0.15 mol) of sulfuric acid (manufactured by Wako Pure Chemical Industries, Ltd.), 415.7 g (4.28 mol) of 35% hydrogen peroxide (manufactured by Wako Pure Chemical Industries, Ltd.), and 25.3 g (0.18 mol) of sodium sulfate (manufactured by Wako Pure Chemical Industries, Ltd.), followed by reaction at 50° C. for 4 hours. Thereafter, the temperature was raised to 70° C. to allow the mixture to react further for 2 hours. After the reaction, the layers were separated to remove an aqueous layer, and an oil layer was washed with ion-exchanged water, a saturated aqueous sodium carbonate solution (manufactured by Wako Pure Chemical Industries, Ltd.), a saturated aqueous sodium sulfite solution (manufactured by Wako Pure Chemical Industries, Ltd.), and 1% saline (manufactured by Wako Pure Chemical Industries, Ltd.), followed by concentration in an evaporator to yield 820 g of an internal epoxide 1.

Production Example B2

(Production of Internal Epoxide Having 18 Carbon Atoms (Internal Epoxide 2))

A flask equipped with a stirrer was charged with the internal olefin 2 (595 g, 2.38 mol) obtained in Production Example A2, 71.7 g (1.20 mol) of acetic acid (manufactured by Wako Pure Chemical Industries, Ltd.), 9.8 g (0.10 mol) of sulfuric acid (manufactured by Wako Pure Chemical Industries, Ltd.), and 324 g (4.00 mol) of 35% hydrogen peroxide (manufactured by Wako Pure Chemical Industries, Ltd.), followed by reaction at 50° C. for 4 hours. Thereafter, the temperature was raised to 80° C. to allow the mixture to react further for 5 hours. After the reaction, the layers were separated to remove an aqueous layer, and an oil layer was washed with ion-exchanged water, a saturated aqueous sodium carbonate solution (manufactured by Wako Pure Chemical Industries, Ltd.), a saturated aqueous sodium sulfite solution (manufactured by Wako Pure Chemical Industries, Ltd.), and ion-exchanged water, followed by concentration in an evaporator to yield 629 g of an internal epoxide 2.

Production Example B3

(Production of Internal Epoxide Having 14 Carbon Atoms (Internal Epoxide 3))

An internal epoxide 3 was obtained in the same manner as in Production Example B1 except that the internal olefin 3 (3.56 mol) obtained in Production Example A3 was used in place of the internal olefin 1 (3.56 mol) obtained in Production Example A1.

Production Example B4

(Production of Internal Epoxide Having 16 Carbon Atoms (Internal Epoxide 4))

An internal epoxide 4 was obtained in the same manner as in Production Example B1 except that the internal olefin 4 (3.56 mol) obtained in Production Example A4 was used in place of the internal olefin 1 (3.56 mol) obtained in Production Example A1.

Production Example B5

(Production of Internal Epoxide Having 18 Carbon Atoms (Internal Epoxide 5))

An internal epoxide 5 was obtained in the same manner as in Production Example B1 except that the internal olefin 5 (3.56 mol) obtained in Production Example A5 was used in place of the internal olefin 1 (3.56 mol) obtained in Production Example A1.

<Production of Reactant of Epoxide and Glycerin (Alkyl Glyceryl Ether, AGE)>

Hereinafter, the alkyl glyceryl ether is referred to as AGE. In addition, AGE1, AGE2, AGE3, AGE4, AGE5, AGE6, AGE7, and the like represent alkyl glyceryl ether 1, alkyl glyceryl ether 2, alkyl glyceryl ether 3, alkyl glyceryl ether 4, alkyl glyceryl ether 5, alkyl glyceryl ether 6, alkyl glyceryl ether 7, and the like, respectively.

Production Example C1

(Production of Reactant of Internal Epoxide 1 and Glycerin (AGE1))

A flask equipped with a stirrer was charged with 2298 g (25.0 mol) of glycerin (manufactured by Wako Pure Chemical Industries, Ltd.) and 0.122 g (1.25 mmol) of 98% sulfuric acid (manufactured by Wako Pure Chemical Industries, Ltd.), and the temperature was raised to 130° C. Thereafter, the internal epoxide 1 (300 g, 1.25 mol) obtained in Production Example B1 was added dropwise over 1 hour, followed by reaction at 130° C./8 hours. Hexane was added to the liquid obtained by this reaction, followed by washing with ion-exchanged water. Subsequently, concentration was performed under reduced pressure in an evaporator to yield 400 g of AGE1. The obtained AGE1 contained 73% ether alcohol 1 in which $R^1$ and $R^2$ each contained an alkyl group having 1 to 13 carbon atoms, the total number of carbon atoms of $R^1$ and $R^2$ was 14, X was a single bond, and A was —O—$CH_2$—CH(OH)—$CH_2$OH in the Chemical Formula (1) (AGE obtained by reacting the hydroxyl group at the 1-position of glycerin with the epoxy group), and 27% ether alcohol 2 in which $R^1$ and $R^2$ each contained an alkyl group having 1 to 13 carbon atoms, the total number of carbon atoms of $R^1$ and $R^2$ was 14, X was a single bond, and A was —O—CH(—CH$_2$—OH)$_2$ in the Chemical Formula (1) (AGE obtained by reacting the hydroxyl group at the 2-position of glycerin with the epoxy group).

Production Example C2

(Production of Reactant of Internal Epoxide 2 and Glycerin (AGE2))

An AGE2 was obtained in the same manner as in Production Example C1 except that the internal epoxide 2 (1.25 mol) obtained in Production Example B2 was used in place of the internal epoxide 1 (1.25 mol) obtained in Production Example B1. The obtained AGE2 contained 72% ether alcohol 1 in which $R^1$ and $R^2$ each contained an alkyl group having 1 to 15 carbon atoms, the total number of carbon atoms of $R^1$ and $R^2$ was 16, X was a single bond, and A was —O—CH$_2$—CH(OH)—CH$_2$OH in the Chemical Formula (1) (AGE obtained by reacting the hydroxyl group at the 1-position of glycerin with the epoxy group), and 28% ether alcohol 2 in which $R^1$ and $R^2$ each contained an alkyl group having 1 to 15 carbon atoms, the total number of carbon atoms of $R^1$ and $R^2$ was 16, X was a single bond, and A was —O—CH(—CH$_2$—OH)$_2$ in the Chemical Formula (1) (AGE obtained by reacting the hydroxyl group at the 2-position of glycerin with the epoxy group).

Production Example C3

(Production of Reactant of Internal Epoxide 3 and Glycerin (AGE3))

An AGE3 was obtained in the same manner as in Production Example C1 except that the internal epoxide 3 (1.25 mol) obtained in Production Example B3 was used in place of the internal epoxide 1 (1.25 mol) obtained in Production Example B1. The obtained AGE3 contained 74% ether alcohol 1 in which $R^1$ and $R^2$ each contained an alkyl group having 1 to 11 carbon atoms, the total number of carbon atoms of $R^1$ and $R^2$ was 12, X was a single bond, and A was —O—CH$_2$—CH(OH)—CH$_2$OH in the Chemical Formula (1) (AGE obtained by reacting the hydroxyl group at the 1-position of glycerin with the epoxy group), and 26% ether alcohol 2 in which $R^1$ and $R^2$ each contained an alkyl group having 1 to 11 carbon atoms, the total number of carbon atoms of $R^1$ and $R^2$ was 12, X was a single bond, and A was —O—CH(—CH$_2$—OH)$_2$ in the Chemical Formula (1) (AGE obtained by reacting the hydroxyl group at the 2-position of glycerin with the epoxy group).

Production Example C4

(Production of Reactant of Internal Epoxide 4 and Glycerin (AGE4))

An AGE4 was obtained in the same manner as in Production Example C1 except that the internal epoxide 4 (1.25 mol) obtained in Production Example B4 was used in place of the internal epoxide 1 (1.25 mol) obtained in Production Example B1. The obtained AGE4 contained 73% ether alcohol 1 in which $R^1$ and $R^2$ each contained an alkyl group having 1 to 13 carbon atoms, the total number of carbon atoms of $R^1$ and $R^2$ was 14, X was a single bond, and A was —O—CH$_2$—CH(OH)—CH$_2$OH in the Chemical Formula (1) (AGE obtained by reacting the hydroxyl group at the 1-position of glycerin with the epoxy group), and 27% ether alcohol 2 in which $R^1$ and $R^2$ each contained an alkyl group having 1 to 13 carbon atoms, the total number of carbon atoms of $R^1$ and $R^2$ was 14, X was a single bond, and A was —O—CH(—CH$_2$—OH)$_2$ in the Chemical Formula (1) (AGE obtained by reacting the hydroxyl group at the 2-position of glycerin with the epoxy group).

Production Example C5

(Production of Reactant of Internal Epoxide 5 and Glycerin (AGE5))

An AGE5 was obtained in the same manner as in Production Example C1 except that the internal epoxide 5 (1.25 mol) obtained in Production Example B5 was used in place of the internal epoxide 1 (1.25 mol) obtained in Production Example B1. The obtained AGE5 contained 73% ether alcohol 1 in which $R^1$ and $R^2$ each contained an alkyl group having 1 to 15 carbon atoms, the total number of carbon atoms of $R^1$ and $R^2$ was 16, X was a single bond, and A was —O—CH$_2$—CH(OH)—CH$_2$OH in the Chemical Formula (1) (AGE obtained by reacting the hydroxyl group at the 1-position of glycerin with the epoxy group), and 27% ether alcohol 2 in which $R^1$ and $R^2$ each contained an alkyl group having 1 to 15 carbon atoms, the total number of carbon atoms of $R^1$ and $R^2$ was 16, X was a single bond, and A was —O—CH(—CH$_2$—OH)$_2$ in the Chemical Formula (1) (AGE obtained by reacting the hydroxyl group at the 2-position of glycerin with the epoxy group).

Production Example C6

(Production of Reactant of C16 Terminal Epoxide and Glycerin (AGE6))

An AGE6 was obtained in the same manner as in Production Example C1 except that 1.25 mol of a C16 terminal epoxide (manufactured by Tokyo Chemical Industry Co., Ltd.) was used in place of the internal epoxide 1 (1.25 mol) obtained in Production Example B1. The obtained AGE6 contained 50% ether alcohol obtained by reacting the hydroxyl group at the 1-position of glycerin with the epoxy group and 50% ether alcohol obtained by reacting the hydroxyl group at the 2-position of glycerin with the epoxy group.

Production Example C7

(Production of Reactant of C18 Terminal Epoxide and Glycerin (AGE7))

An AGE7 was obtained in the same manner as in Production Example C1 except that 1.25 mol of a C18 terminal epoxide (manufactured by Tokyo Chemical Industry Co., Ltd.) was used in place of the internal epoxide 1 (1.25 mol) obtained in Production Example B1. The obtained AGE7 contained 51% ether alcohol obtained by reacting the hydroxyl group at the 1-position of glycerin with the epoxy group and 49% ether alcohol obtained by reacting the hydroxyl group at the 2-position of glycerin with the epoxy group.

Examples 1 to 4 and Comparative Examples 1 to 5

The following measurement and evaluation were performed using the respective products produced in Production Examples C1 to C7. The results are shown in Table 1.
<Measurement of Melting Point>

Using a high sensitivity differential scanning calorimeter (manufactured by Hitachi High-Tech Science Corporation, trade name: DSC7000X), each of the products produced in Production Examples C1 to C7 was placed in a 70 μL pan, the temperature was raised from −60° C. to 80° C. at 2° C./min, and the temperature at the maximum peak of the temperature difference detected by the differential thermal electrode with respect to the temperature raising time was defined as the melting point.
<Preparation of Hexane Solution>

To 100 mL of hexane, 5.0 g of each of the products produced in Production Examples C1 to C7 was added, followed by sufficient stirring to prepare a hexane solution.
<Evaluation of Appearance of Hexane Solution>
After the hexane solution was prepared by the above method, the hexane solution was allowed to stand at 25° C. for 1 hour, and then the appearance of the hexane solution was visually observed and evaluated according to the following criteria.

○: The solution is transparent.
X: The compound is precipitated in the solution.
<Measurement of Contact Angle>

A slide glass (76 mm×26 mm×1 mm) was immersed in the hexane solution prepared by the above method for 10 seconds, then immersed in 5 mL of hexane for 10 seconds, and dried with hot air at 120° C. for 10 seconds. Thereafter, the slide glass was horizontally placed on the stage of a contact angle meter (DM-701 manufactured by Kyowa Interface Science Co., Ltd.), 2 μL of ion-exchanged water was dropped onto the placed slide glass with a syringe, and the contact angle was measured after 5 seconds.

Comparative Example 4 in Table 1 shows the contact angle measured in the same manner except that hexane was used in place of the hexane solution.
<Foaming>

In a 100 mL screw tube, 0.5 g of each of the products produced in Production Examples C1 to C5, 10 g of dibutylene glycol, and 39.5 g of ion-exchanged water were put and shaken for 30 seconds. After 0 seconds and 30 seconds, the heights of foam from the liquid surface were measured.

In Comparative Example 5 in Table 1, the height of foam was measured in the same manner as described above, except that the respective products produced in Production Examples C1 to C5 were not added.

TABLE 1

| | Production Example | Compound | Content ratio of compound in which $R^1$ has 5 or more carbon atoms and $R^2$ has 5 or more carbon atoms (%) | Melting point (° C.) | Appearance of hexane solution | Contact angle (°) | Height of foam (mm) After 0 seconds | Height of foam (mm) After 30 seconds |
|---|---|---|---|---|---|---|---|---|
| Example 1 | Production Example C-1 | AGE1 | 36.5 | −18 | ○ | 62.0 | 84 | 8 |
| Example 2 | Production Example C-2 | AGE2 | 45.1 | 1 | ○ | 66.6 | 102 | 34 |
| Example 3 | Production Example C-4 | AGE4 | 22.1 | −10 | ○ | 61.3 | 100 | 30 |
| Example 4 | Production Example C-5 | AGE5 | 26.6 | 16 | ○ | 65.2 | 122 | 70 |
| Comparative Example 1 | Production Example C-3 | AGE3 | 13.6 | −57 | ○ | 34.0 | 0 | 0 |
| Comparative Example 2 | Production Example C-6 | AGE6 | 0 | 36 | × | 28.1 | — | — |
| Comparative Example 3 | Production Example C-7 | AGE7 | 0 | 51 | × | 35.1 | — | — |
| Comparative Example 4 | — | — | — | — | — | 8.5 | — | — |
| Comparative Example 5 | — | — | — | — | — | — | 66 | 0 |

From Table 1, it is found that the products of Examples 1 to 4 have low melting points and are soluble in an organic solvent. In addition, it is also found that the products of Examples 1 to 4 have high contact angles with water and form a hydrophobic coating which is hardly wetted with water. On the other hand, it is found that the products of Comparative Examples 1 to 3 have low contact angles with water, and the hydrophobicity of the formed coatings is low. It is also found that the products of Comparative Examples 2 and 3 have high melting points and are hardly soluble in an organic solvent.

From Table 1, it is also found that the products of Examples 1 to 4 foam well. It is also found that, comparing Example 1 with Example 3, and Example 2 with Example 4, the compound represented by the Chemical Formula (1) has better foam retention when the content ratio of the compound in which $R^1$ has 5 or more carbon atoms and $R^2$ has 5 or more carbon atoms is (20% or more and) 30% or less. On the other hand, it is found that the product of Comparative Example 1 does not foam.

INDUSTRIAL APPLICABILITY

The ether alcohol or the composition of the present invention is suitably used as a raw material for a surfactant, an emulsifier, a dispersant, a polymer, a resin, and the like, an additive for an oil agent such as a lubricating oil, a paint additive, an agrochemical additive, a resin additive, a metal surface modifier, a cosmetic base material, a medical auxiliary, a fiber oil agent, a petroleum agent, a processing agent, a lubricant, a plasticizer, an emulsifier, a dispersant, an antifogging agent, an antistatic agent, and an antifoaming agent.

The invention claimed is:

1. A compound represented by a Chemical Formula (1):

[Chemical Formula (1)]

wherein $R^1$ and $R^2$ are each an aliphatic hydrocarbon group having 1 or more and 33 or less carbon atoms, a total number of carbon atoms of $R^1$ and $R^2$ is 14 or more and 34 or less, X is a single bond or an aliphatic hydrocarbon group having 1 or more and 5 or less carbon atoms, and A is —O—$CH_2$—CH(OH)—$CH_2$OH or —O—CH(—$CH_2$—OH)$_2$.

2. The compound according to claim 1, wherein in the compound represented by the Chemical Formula (1), X is a single bond.

3. The compound according to claim 1, wherein the compound represented by the Chemical Formula (1) comprises two or more kinds of the compound between which total numbers of carbon atoms of $R^1$ and $R^2$ are the same, but numbers of carbon atoms of $R^1$ and numbers of carbon atoms of $R^2$ are each different.

4. The compound according to claim 3, wherein in the compound represented by the Chemical Formula (1), a content ratio of a compound in which $R^1$ has 5 or more carbon atoms and $R^2$ has 5 or more carbon atoms is 10 mass % or more and 90 mass % or less with respect to a total amount of the compound represented by the Chemical Formula (1).

5. The compound according to claim 1, wherein the compound represented by the Chemical Formula (1) comprises a compound 1 in which A is —O—$CH_2$—CH(OH)—$CH_2$OH and a compound 2 in which A is —O—CH(—$CH_2$—OH)$_2$.

6. The compound according to claim 5, wherein in the compound represented by Chemical Formula (1), a content of the compound 1 with respect to a total amount of the compound 1 and the compound 2 is 30 mass % or more.

7. The compound according to claim 1, wherein in the compound represented by Chemical Formula (1), a total content of a compound in which a total number of carbon atoms of $R^1$ and $R^2$ is 14 and a compound in which a total number of carbon atoms of $R^1$ and $R^2$ is 16 is 75 mass % or more.

8. The compound according to claim 1, wherein the compound represented by the Chemical Formula (1) has a melting point of 30° ° C. or lower.

9. The compound according to claim 1, wherein the compound represented by the Chemical Formula (1) is a reactant of an internal epoxide and glycerin.

10. The compound according to claim 9, wherein the internal epoxide is an oxide of an internal olefin, and the internal olefin contains 5 mass % or less of a terminal olefin.

11. A composition comprising the compound according to claim 1.

12. The composition according to claim 11, wherein a content of the compound represented by the Chemical Formula (1) is 50 mass % or more.

13. The composition according to claim 11, further comprising water.

14. The compound according to claim 2, wherein the compound represented by the Chemical Formula (1) comprises two or more kinds of the compound between which total numbers of carbon atoms of $R^1$ and $R^2$ are the same, but numbers of carbon atoms of $R^1$ and numbers of carbon atoms of $R^2$ are each different.

15. The compound according to claim 2, wherein the compound represented by the Chemical Formula (1) comprises a compound 1 in which A is —O—$CH_2$—CH(OH)—$CH_2$OH and a compound 2 in which A is —O—CH(—$CH_2$—OH)$_2$.

16. The compound according to claim 3, wherein the compound represented by the Chemical Formula (1) comprises a compound 1 in which A is —O—$CH_2$—CH(OH)—$CH_2$OH and a compound 2 in which A is —O—CH(—$CH_2$—OH)$_2$.

17. The compound according to claim 4, wherein the compound represented by the Chemical Formula (1) comprises a compound 1 in which A is —O—$CH_2$—CH(OH)—$CH_2$OH and a compound 2 in which A is —O—CH(—$CH_2$—OH)$_2$.

18. The compound according to claim 2, wherein in the compound represented by Chemical Formula (1), a total content of a compound in which a total number of carbon atoms of $R^1$ and $R^2$ is 14 and a compound in which a total number of carbon atoms of $R^1$ and $R^2$ is 16 is 75 mass % or more.

19. The compound according to claim 3, wherein in the compound represented by Chemical Formula (1), a total content of a compound in which a total number of carbon atoms of $R^1$ and $R^2$ is 14 and a compound in which a total number of carbon atoms of $R^1$ and $R^2$ is 16 is 75 mass % or more.

20. The compound according to claim 4, wherein in the compound represented by Chemical Formula (1), a total content of a compound in which a total number of carbon atoms of $R^1$ and $R^2$ is 14 and a compound in which a total number of carbon atoms of $R^1$ and $R^2$ is 16 is 75 mass % or more.

\* \* \* \* \*